(12) United States Patent
Park et al.

(10) Patent No.: US 8,445,212 B2
(45) Date of Patent: May 21, 2013

(54) MICROFLUIDIC STRUCTURE FOR DETECTING BIOMOLECULE AND MICROFLUIDIC DEVICE COMPRISING THE SAME

(75) Inventors: Jong Myeon Park, Incheon-si (KR); Won Yong Lee, Seoul (KR); Han Nim Choi, Seoul (KR); Jung Hoon Lee, Jinju-si (KR)

(73) Assignees: Samsung Electronics Co., Ltd., Suwon-si (KR); Industry-Academic Cooperation Foundation, Yonsei University, Seoul (KR)

( * ) Notice: Subject to any disclaimer, the term of this patent is extended or adjusted under 35 U.S.C. 154(b) by 170 days.

(21) Appl. No.: 12/874,560

(22) Filed: Sep. 2, 2010

(65) Prior Publication Data

US 2011/0124118 A1 May 26, 2011

(30) Foreign Application Priority Data

Nov. 24, 2009 (KR) ................................ 2009-113812

(51) Int. Cl.
*G01N 33/53* (2006.01)

(52) U.S. Cl.
USPC ........... 435/7.1; 427/2.11; 436/518; 436/525; 435/287.1

(58) Field of Classification Search
None
See application file for complete search history.

(56) References Cited

U.S. PATENT DOCUMENTS

| 2001/0055812 | A1* | 12/2001 | Mian et al. | 436/45 |
| 2002/0010279 | A1* | 1/2002 | Satcher et al. | 525/255 |
| 2002/0164811 | A1* | 11/2002 | Hud et al. | 436/67 |
| 2002/0192722 | A1* | 12/2002 | Stolowitz et al. | 435/7.9 |

* cited by examiner

*Primary Examiner* — N. C. Yang
(74) *Attorney, Agent, or Firm* — Sughrue Mion, PLLC

(57) ABSTRACT

Disclosed are a micro-fluidic structure for detecting biomolecules and a micro-fluidic device having the same. More particularly, a target material including at least two cis-diols is detected by a first material containing a boronate moiety and a second material containing another boronate moiety while generating electrical signals.

27 Claims, 10 Drawing Sheets

HbA₁c

MICROFLUIDIC STRUCTURE FOR DETECTING BIOMOLECULE AND MICROFLUIDIC DEVICE COMPRISING THE SAME

CROSS-REFERENCE TO RELATED APPLICATION

This application claims the priority from Korean Patent Application No. 2009-113812 filed on Nov. 24, 2009 with the Korean Intellectual Property Office, the disclosure of which is incorporated herein by reference.

BACKGROUND

1. Field

Embodiments relate to a micro-fluidic structure for detecting biomolecules and a micro-fluidic device having the same and, more particularly, to a micro-fluidic structure wherein a first sample chamber contains a target material having at least two cis-diols, a second sample chamber contains a second material including a boronate moiety and generating electrical signals, a reaction chamber contains a first material in a fixed state which includes another boronate moiety bound to a first cis-diol of the target material, channels connect the chambers to one another, and valves open and close the channels and, in addition, a centrifugal micro-fluidic device including the same.

2. Description of the Related Art

In order to flow and move a fluid in a micro-fluidic structure in a micro-fluidic device, a driving force is generally required. As such a driving force, capillary pressure or pressure generated using an additional pump may be used. In recent years, clinical diagnosis analyzers designed to enable detection of a target material present in a small amount of fluid in simple and economical ways including, for example, a centrifugal micro-fluidic device having a micro-fluidic structure mounted on a circular disk type rotational platform such as lab-on-a disk and/or a lab CD have been proposed.

Lab-on-a disk (or 'laboratory on a disk' is a CD type device in which various components are integrated for analysis of biomolecules used. When introducing a bio sample such as blood to the micro-fluidic structure of the disk, a fluid such as a sample, a chemical reagent, etc. may be transferred to a desired location simply by applying centrifugal force without additional driving systems such as driving pressure in order to transport the fluid.

In order to more effectively analyze a biomolecule containing at least two cis-diols in the molecule by a disk type analyzer, there still is a need for improvements in designing a disk provided with multiple chambers.

SUMMARY

Exemplary embodiments provides a micro-fluidic structure for detecting a biomolecule having at least two cis-diols, wherein a material labeled or marked with a biomolecule specific antibody is not used but, instead, another material reacting with a cis-diol and generating electrical signals is used to detect the biomolecule concurrently with reaction thereof. In addition, another exemplary embodiment provides a centrifugal micro-fluidic device having a rotational body as well as the micro-fluidic structure described above.

According to an aspect of the present invention, there is provided a micro-fluidic structure, including: a reaction chamber that contains an immobilized first material, the first material comprising a boronate moiety which is capable of binding to a cis-diol group of the target material; a first chamber that contains a second material comprising a boronate moiety which is capable of binding to another cis-diol group of the target material; and generating a detectable signal; channels through which the chambers are fluid communicative to one another; and valves for opening and closing the channels to control the flow of a fluid in the micro-fluidic structure.

In this regard, the boronate moiety in the first material may be selected from a group consisting of boric acid, boronic acid and, boronate compounds.

The boronate compound may be a phenylboronic acid, boronate esters or boronate salts.

An inner surface of the reaction chamber may be made of a silicon wafer, silicone, glass, quartz, metal and/or plastic material.

Such inner surface of the reaction chamber may comprise gold, silver, platinum, aluminum and/or copper.

The target material having at least two cis-diols may be a glycoprotein or carbohydrate.

Such glycoprotein may be selected from a group consisting of glycated hemoglobin, fibrinogen, RNase, human a1-acid glycoprotein (or human alpha-1-acid glycoprotein), fetuin and horseradish peroxidase.

Such carbohydrate may be selected from a group consisting of β-D-glucose, β-D-galactose, β-D-mannose, α-L-fucose, N-acetylgalactosamine, N-acetylglucosamine, N-acetylneuraminic acid and xylose.

The second material, which has a boronate moiety capable of binding to the target material and can emit a detectable signal, may be selected from a group consisting of ferrocene boronate, ferrocene boronate derivatives, boronate ferricyanide, boronate ferrocyanide, ruthenium complexes including a boronate moiety, luminol including a boronate moiety, and lucigenin including a boronate moiety.

Also, the detectable signal may be an electrical signal.

The micro-fluidic structure may further comprise a second chamber which receives a sample containing the target material, the target material having at least two cis-diol groups.

The first material may be coupled to an inner surface of the reaction chamber, or bonded to the outer surface of a bead, a microsphere, a nanoparticle, a membrane, a film, or a porous matrix.

According to another embodiment, there is provided a centrifugal micro-fluidic device which includes a rotational body and the micro-fluidic structure described above, wherein a fluid contained in the micro-fluidic structure is transported using centrifugal force generated by rotation of the rotational body.

According to a still further embodiment, there is provided a method for detection of a target material containing at least two cis-diols using the micro-fluidic device described above, which includes: adding a sample containing the target material that contains at least two cid-diols to a reaction chamber, so as to combine a first cis-diol of the target material with a boronate moiety of a first material fixed to the reaction chamber; adding a sample including a second material to the reaction chamber, so as to combine a second cis-diol of the target material with another boronate moiety of the second material; and measuring electrical signals generated from the second material.

In another embodiment, the method for detection of a target material containing at least two cis-diol groups using the micro-fluidic device as described above, includes steps of providing the micro-fluidic device described above; bringing a sample containing the target material that contains at least two cis-diol groups to be in contact with the immobilized first material, thereby one of the at least two cis-diol groups of the target material binds to the boronate moiety of the immobilized first material in the reaction chamber to form an immobilized first material-target material complex; bringing the second material to be contact with the target material bound to the immobilized first material, thereby the boronate moiety of the second material binds to another cis-diol group of the at least two cis-diol groups of the target material of the immobilized first material-target material complex; and measuring a signal generated from the second material bound to the immobilized first material-target material complex.

In such methods, a washing process for removal of unreacted and/or non-reactive materials may be carried out between respective processes.

BRIEF DESCRIPTION OF THE DRAWINGS

These and/or other embodiments will become apparent and more readily appreciated from the following description of the embodiments, taken in conjunction with the accompanying drawings of which.

DETAILED DESCRIPTION

Hereinafter, advantageous features and characteristics of the embodiments and practical methods thereof will be clearly understood by the following detailed description for preferred and illustrative embodiments with reference to the accompanying drawings. However, at least one exemplary embodiment may be embodied in other various forms, which are not particularly restricted to those described herein.

A micro-fluidic structure for detection of biomolecules and a micro-fluidic device using the same according to the exemplary embodiment are generally based on a principle wherein a boronic acid binds to a hydroxyl group in cis-diol of a material containing carbohydrate chains.

A target material to be detected is a compound containing at least two cis-diols. Examples of such compound may include a glycoprotein or carbohydrate that has at least two cis-diols.

Figure 2:
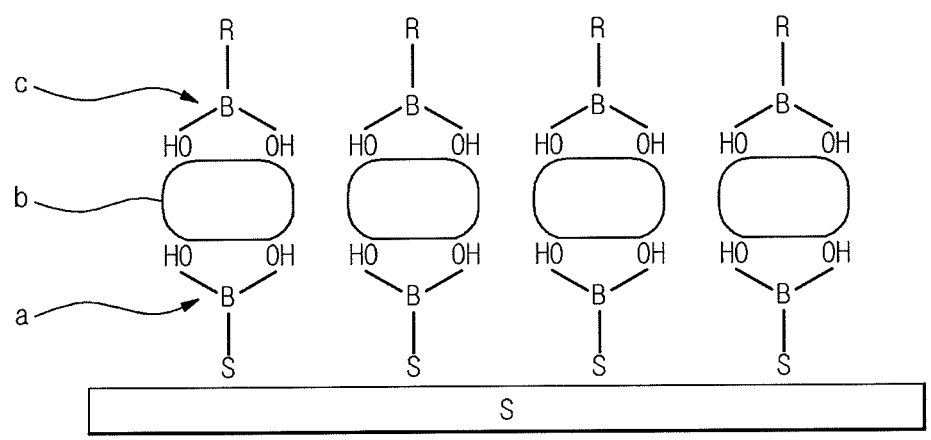
FIG. 2 is an illustrative diagram explaining a principle of detecting a target material in a micro-fluidic device according to an exemplary embodiment.

FIG. 2 is an illustrative diagram explaining a detection principle of a target material by a micro-fluidic device according to an embodiment. First cis-diol of at least two cis-diols of a target material (b) (i.e., glycoprotein and/or carbohydrate having at least two cis-diols) binds to a first boronate moiety (a) immobilized to a substrate S, while a second cis-diol of the target material (b) binds to a second boronate moiety (c), so as to form a sandwiched product wherein the target material (b) is coupled to a boronate moiety at both ends thereof. As the second boronate moiety can generate a detectable signal generating, the target material (b) may be detected by measuring the signal (e.g., electrical signal) generated by the second boronate moiety (c) coupled to the target material (b).

According to an aspect of the present invention, a micro-fluidic structure comprises: a first chamber that receives a target material having at least two cis-diols; a second chamber that contains a second material including a boronate moiety and generating electrical signals; a reaction chamber that contains an immobilized first material comprising a boronate moiety; channels through which the chambers are connected to one another; and valves for opening and closing the channels.

Figure 1:
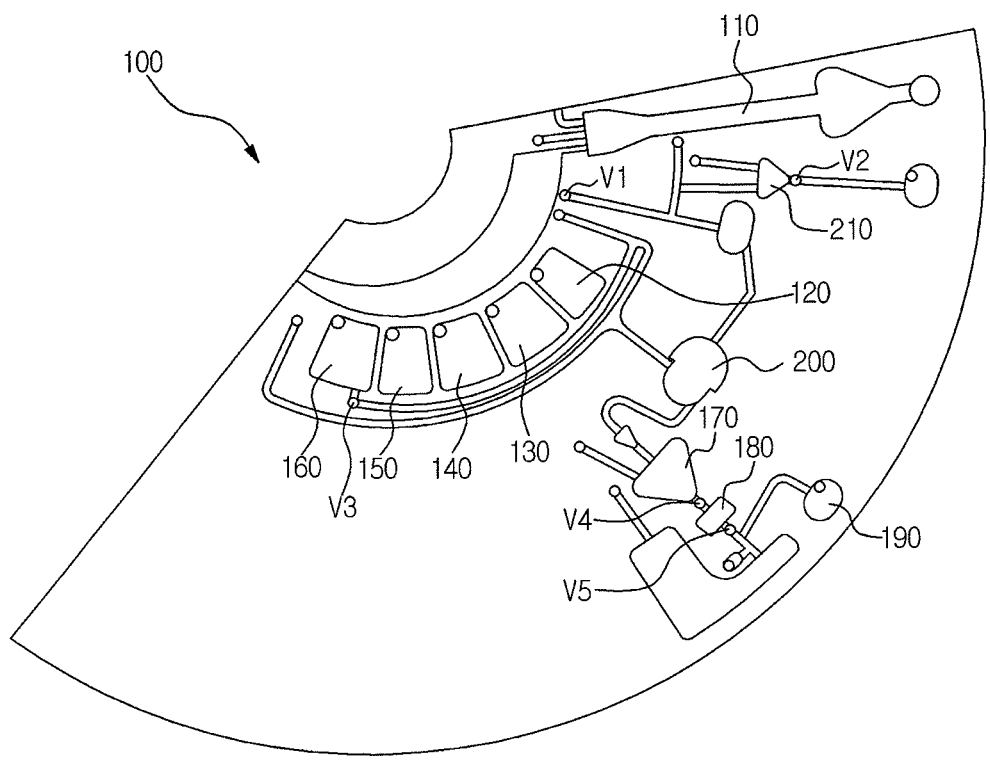
FIG. 1 is a schematic view illustrating a structure of a micro-fluidic device according to an exemplary embodiment.

FIG. 1 is a schematic view illustrating a structure of a micro-fluidic device according to an aspect of the present invention.

As shown in FIG. 1, the micro-fluidic device 100 according to an embodiment is a centrifugal force type micro-fluidic device comprising a micro-fluidic structure wherein the structure has a zone in which a first material having a boronate moiety capable of binding to a target material is fixed to a reaction chamber. In this case, such a zone may partially or entirely constitute an inner surface of the reaction chamber.

FIG. 1 illustrates a configuration of an exemplary embodiment of the micro-fluidic device, comprising: chambers 140 and 150 in which various analytical buffers are stored; other chambers for conducting biological and/or chemical reactions; a chamber 110 which receives and accommodates a target material; fluid channels through which fluid samples and buffers are transported; and valves for opening and closing the fluid channels. The valve may be installed in the chamber or in a channel connected between the chambers, thereby controlling fluid transfer between the chambers. Thus, the microfluidic device may further include valve that is operably connected to the chamber. For example, a valve V1 may be located between the first sample chamber 110 and the reaction chamber 170. The valve V1 controls flow of the sample in the channel between the sample chamber 110 and the reaction chamber 170. The valves may be any one selected from different types of micro-fluidic valves. The valves may comprise, for example, a normally closed valve wherein a channel of the valve is closed to prevent a fluid from flowing unless the valve opens by external power.

Referring to FIG. 1, a rotational body used in the exemplary embodiment of the present invention may comprise a circular disk type platform. Such a platform is easily fabricated and a surface of the platform may be formed using biologically inactive acryl or plastic materials. However, the material for fabrication of the rotational body is not particularly limited and may include any materials with chemical or biological stability, optical transparency, and/or mechanical workability.

The rotational body may be fabricated using at least one selected from a variety of materials such as plastic, polymethylmethacrylate (PMMA), glass, mica, silica, or a silica wafer material. Preferably, the plastic material is used in view of economic merits and easy workability. Useful plastic materials may include polypropylene, polyacrylate, polyvinylalcohol, polyethylene, polymethylmethacrylate, polycarbonate, etc. In one embodiment, polypropylene or polycarbonate are used.

A micro-fluidic structure may be located on the rotational body, and may have a configuration wherein a first sample chamber 110 receives a target material comprising at least two cis-diols, a second sample chamber 130 contains a second material including a second boronate moiety and generating a detectable signal such as fluorescence or luminescence, a reaction chamber 170 contains a first material including a first boronate moiety which binds to a first cis-diol of the target material, channels connect the chambers to one another, and valves open and close the channels. The first boronate moiety and the first boronate moiety may be different from each other. In one embodiment, the first boronate moiety does not generate a detectable signal and the second boronate moiety generates a detectable signal. In another embodiment, the first boronate moiety and the second boronate moiety each may generate a detectable signal, which is different from each other.

Such a micro fluidic structure may further comprise buffer chambers 140 and 150 and another chamber 200 that contains a ferricyanide/ferrocyanide solution required for conducting cyclic voltammetry (CV) in order to sense electrical signals, in addition to the foregoing first and second sample chambers 110 and 130 (FIG. 1).

The reaction chamber 170 may be fabricated in any form selected from bead, microsphere, nanoparticle, gel, membrane, film, porous matrix and microchannel. An inner surface of the reaction chamber 170 may be formed using a silicon wafer, silicone, glass, quartz or plastic material. Also, the inner surface of the reaction chamber may comprise gold, silver, platinum, aluminum or copper.

After fabricating the inner surface of the reaction chamber 170 with a silicon wafer, glass, quartz or plastic material, the fabricated inner surface may be further coated with gold, silver, platinum, aluminum or copper. In this case, the inner surface of the reaction chamber 170 may be used as an electrode for measuring electrical signals.

The first material may be immobilized to the inner surface of the reaction chamber 170 by any conventional methods such as chemical, physical or electrochemical processes. For instance, the first material may be immobilized to the reaction chamber 170 according to vacuum filtering, self-assembly, a Langmuir-Blodgett method, solution casting, bar coating, immersion coating, spin coating, injecting coating, and/or a roll-to-roll process, without particular limitation thereto.

A "target material" described herein means a substance to be detected, for example, a bio-molecular material found in a living body. Such a target material, according to an exemplary embodiment, may comprise a biomolecule having at least two cis-diol groups. The biomolecule having at least two cis-diol groups may be a glycoprotein and/or carbohydrate having at least two cis-diols.

The glycoprotein may include, for example, glycated hemoglobin, fibrinogen, RNase B, human a1-acid glycoprotein, fetuin or horseradish peroxidase, without particular limitation thereto.

The carbohydrate may include, for example, β-D-glucose, β-D-galactose, β-D-mannose, α-L-fucose, N-acetylgalactosamine, N-acetylglucosamine, N-acetylneuraminic acid or xylose, without particular limitation thereto.

The target biomolecule is an analyte and the first material immobilized onto the reaction chamber is a material which is capable of covalently binding to a hydroxyl group of the cis-diol in the target biomolecule in order to capture the target biomolecule. The first material contains a boronate moiety selected from a group consisting of boric acid, boronic acid and boronate compounds. Also, the boronate compound is boronate esters, boronate salts or phenylboronic acid. Examples of the first material including the boronate moiety may be 4-carboxyphenylboronic acid, 3-nitro-5-carboxy phenylboronic acid, m-aminophenylboronic acid, 4-mercaptophenylboronic acid, thiophene-3-boronic acid or a phenylboronic acid terminated alkanethiol although the present invention is not particularly limited thereto.

Figure 4:
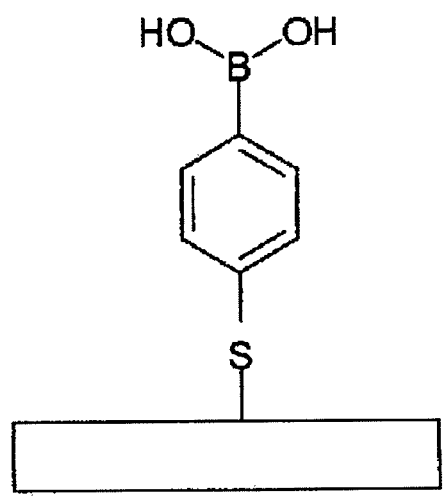
FIG. 4 illustrates 4-mercaptophenylboronic acid immobilized to an inner surface of a reaction chamber according to an exemplary embodiment.
Figure 5:
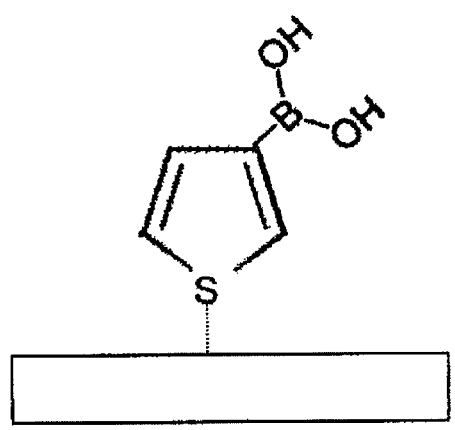
FIG. 5 illustrates thiophene-3-boronic acid immobilized to an inner surface of a reaction chamber according to an exemplary embodiment.
Figure 6:
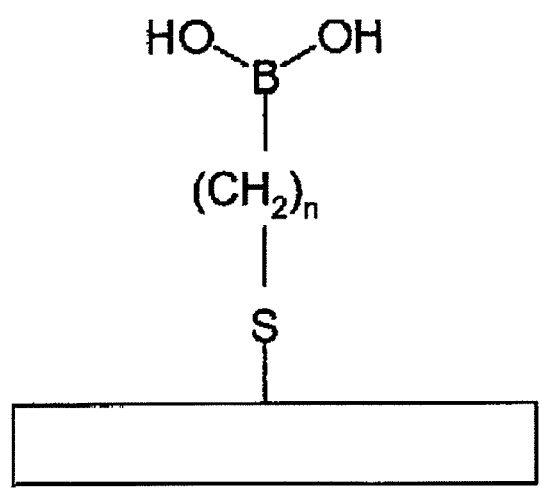
FIG. 6 illustrates a phenylboronic acid terminated alkanethiol immobilized to an inner surface of a reaction chamber according to an exemplary embodiment.

For instance, FIG. 4 illustrates 4-mercaptophenylboronic acid fixed to an inner surface of the reaction chamber 170. Likewise, FIGS. 5 and 6 illustrate thiophene-3-boronic acid and a phenylboronic acid terminated alkanethiol immobilized to the inner surface of the reaction chamber 170, respectively. Each boronate moiety (HO—B—OH) shown in FIGS. 4 to 6 is bound to a first cis-diol of the target material, so as to immobilize the target material to the inner surface of the reaction chamber 170.

Figure 3:
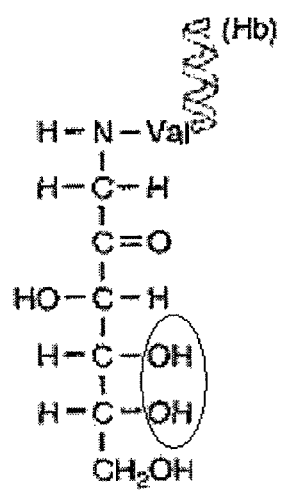
FIG. 3 is a schematic view illustrating a structure of glycated (or glycosylated) hemoglobin as an exemplary glycoprotein.

A representative target material is glycated hemoglobin. FIG. 3 schematically illustrates a partial structure of the glycated hemoglobin ($HbA_{1c}$), in which glucose is bound to valine of hemoglobin (Hb). The cis-diol groups of the glycated hemoglobin is circled. Glycated hemoglobin is known as a precise index indicating an average blood sugar level of a person measured over a period of 2 to 3 months and is a very important biomolecule for control of a glucose level in blood of a diabetic patient.

Various methods for measurement of glycated hemoglobin in blood have been developed. There are conventional known methods such as ion exchange chromatography, affinity chromatography, electrophoresis, complicated coloring, etc. which are commercially available, however, such methods are complicated, have difficulties in use and entail techniques requiring a high skill level. Alternatively, an immunological method using a specific antibody to recognize an N-terminated peptide residue of glycated hemoglobin was developed to quantitatively determine the glycated hemoglobin. However, this method has restrictions in performance wherein the antibody must identify a glycated portion of the glycated hemoglobin with high sensitivity and the glycated hemoglobin must be modified in order to enable identification of the glycated portion by the antibody. In addition, the above method entails a problem wherein a turbidity test comprising reaction of polyhapten having multiple antigen epitopes and detection thereof is required, since it is difficult to form an antigen-antibody complex.

According to another embodiment, the glycated hemoglobin may be easily detected by combining a boronate moiety with a hydroxyl group of cis-diol present in the glycated hemoglobin without modification of the glycated hemoglobin and/or use of specific antigens for the glycated hemoglobin. The micro-fluidic structure according to the aspect of the present invention may detect glycoprotein or carbohydrate containing at least two cis-diols, without particular limitation to the glycated hemoglobin. As shown in FIG. 3, the glycated hemoglobin has cis-diols bound on two β-chains, respectively, in an HbA1c form wherein glucose is covalently bound to a β-chain based valine terminated amine. That is, when a first cis-diol of a target material is bound to a boronate moiety of a first material and fixed to a surface of the reaction chamber 170 while a second cis-diol of the target material is directly bound to a second material generating electrical signals, the target material can be detected by measuring the electrical signals.

The second material is capable of binding to the second cis-diol of the target material and generates electrical signals. More particularly, the second material may comprise boronate generating electrical signals and such boronate may include, for example, ferrocene boronate, ferrocene boronate derivatives, boronate ferricyanide, boronate ferrocyanide, ruthenium complexes including the boronate moiety, luminol including the boronate moiety, and lucigenin including the boronate moiety and the like without particular limitation thereto. When the second material is bound to the second cis-diol of the target material, an electrochemical reaction occurs which in turn enables a specific cyclic voltammogram (CV), thereby detecting the presence and/or amount of biomolecules.

In consideration of a passage for transportation of a fluid by centrifugal force, the chambers of the micro-fluidic structure are preferably arranged in the rotational body wherein the chambers containing buffers and a sample containing the target material are positioned nearest a center axis of the rotational body, the reaction chamber is present farthest from the same, and the second reaction chamber is preferably aligned therebetween.

According to another aspect of the present invention, there is provided a centrifugal type micro-fluidic device comprising the rotational body and the micro-fluidic structure described above, wherein a fluid contained in the micro-fluidic structure is transported using centrifugal force caused by rotation of the rotational body.

According to another aspect of the present invention, there is provided a method for detection of a target material having at least two cis-diols using the micro-fluidic device described above, which comprises: adding a sample including the target material that contains at least two cis-diols to a reaction chamber, so as to combine a first cis-diol of the target material with a boronate moiety of a first material fixed to the reaction chamber; adding a sample including a second material to the reaction chamber, so as to combine a second cis-diol of the target material with another boronate moiety of the second material; and measuring electrical signals generated from the second material.

According to the foregoing method, the target material may be detected in the reaction chamber while measuring electrical signals of the second material.

The above method may further include a washing process to remove unreacted or non-reactive materials between individual processes described above.

Initially, the first material including a boronate moiety which binds to a hydroxyl group of the cis-diol is immobilized to an inner surface of the reaction chamber 170. Here, the immobilized first material may be adhered without a particular sequential order thereof. The first material may be fixed to the inner surface of the reaction chamber 170 by any conventional method including chemical, physical and/or electrochemical processes. Examples of the method include vacuum filtering, self-assembly, a Langmuir-Blodgett method, solution casting, bar coating, immersion coating, spin coating, injection coating, a roll-to-roll process, etc., although the method is not particularly limited thereto.

A sample including a target material having at least two cis-diols is placed in the first sample chamber 110 and another sample including a second material that includes a boronate moiety and generates electrical signals is placed in the second sample chamber 130.

A buffer is charged in the buffer chambers 140 and 150. The buffer may comprise a general buffer solution for detection of biomolecules. For example, the buffer may be phosphate buffered saline (hereinafter, referred to as 'PBS').

In order to conduct cyclic voltammetry (CV) for measuring electrical signals described below, a ferricyanaide/ferrocyanaide solution is introduced into the chamber 200.

Then, according to centrifugal force caused by rotation of a disk type rotational body, the sample containing the target material stored in the first sample chamber 110 is transported to the reaction chamber. Here, a hydroxyl group of a first cis-diol present in the target material included in the sample transported to the reaction chamber 170 is bound to the boronate moiety fixed to the reaction chamber 170. Then, uncombined residue is removed by washing the reaction chamber 170.

Afterward, the second material in the second sample chamber 130 is transported to the reaction chamber 170 using centrifugal force. In the reaction chamber 170, a boronate moiety included in the second material is bound to a hydroxyl group of a second cis-diol present in the target material fixed to the inner surface of the reaction chamber 170. After completing such combination of the second material with the target material, electrical signals of the second material may be measured using a ferricyanide/ferrocyanide solution required for CV in order to detect electrical signals in the chamber 200, thereby detecting the target material.

EXAMPLE 1

Immobilization of Boronate Moiety to Inner Surface of Reaction Chamber

An inner surface of a gold coated reaction chamber was repeatedly washed using distilled water for 5 minutes, ethanol for 5 minutes, acetone for 3 minutes, and finally using distilled water again for 5 minutes, so as to completely eliminate impurities.

4-Mercaptophenylboronic acid purchased from Aldrich was dissolved in a mixed solution of distilled water and ethanol (ethanol:distilled water=1:9) to prepare a 5 mM diluted solution. An electrode was placed in the prepared solution, a solution immersion self-assembly process was carried out for 16 hours to form a self-assembled monolayer (hereinafter, referred to as 'SAM'), and a boronate moiety was immobilized to the inner surface of the reaction chamber. As shown in FIG. 4, 4-mercaptophenylboronic acid was immobilized to the inner surface of the reaction chamber.

In order to identify whether an SAM was formed, CV was measured. CVs before the immobilization of the boronate moiety and after formation of SAM of the boronate moiety were measured, respectively. For each of these cases, the chamber was washed with a PBS buffer (pH 7), 30 cycles, at an applied potential of 0.5V to −0.15V and a scan rate of 100 mV/s. Using a ferricyanide or ferrocyanide solution (5 mM, pH8), a CV of the inner surface of the washed reaction chamber was measured at an applied potential of 0.5V to −0.15V and a scan rate of 100 mV/s.

Figure 7:
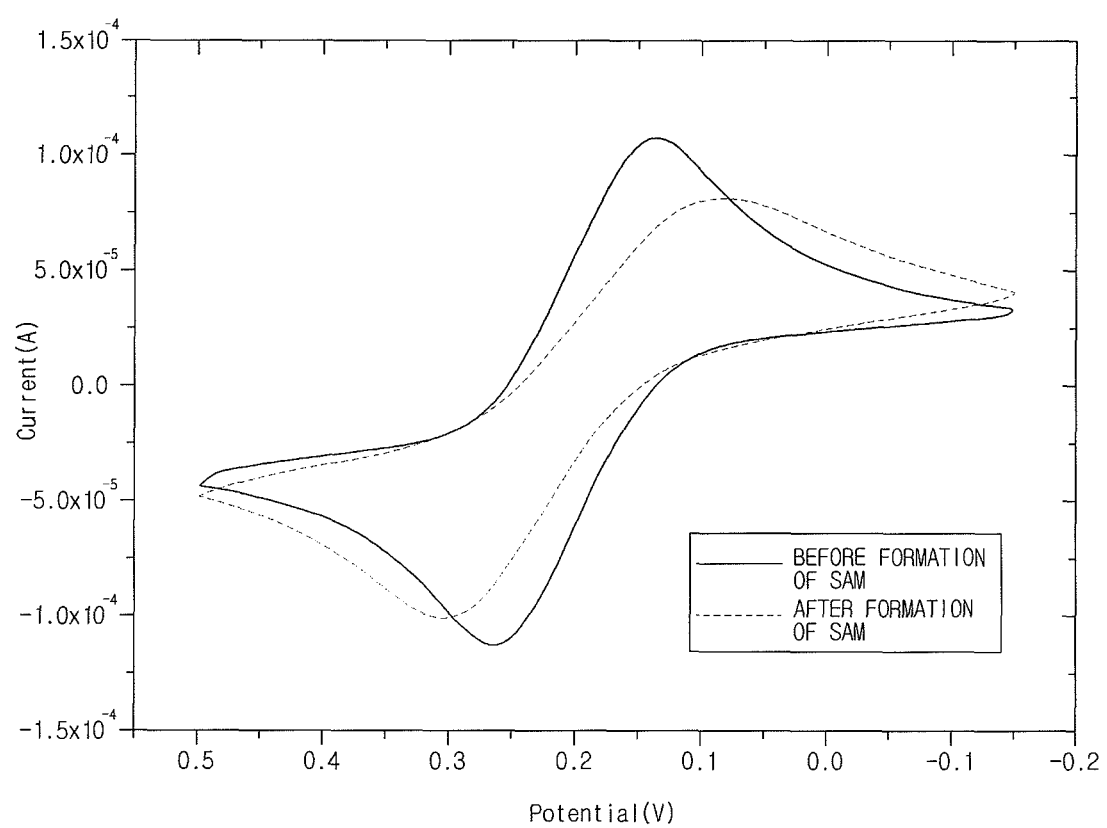
FIG. 7 is cyclic voltammograms (CVs) measured from an inner surface of a reaction chamber before and after formation of a self-assembly monolayer (SAM) of boronate moiety according to an exemplary embodiment.

The measured results are shown in FIG. 7. That is, FIG. 7 is cyclic voltammograms (CVs) measured from the inner surface of the reaction chamber before and after formation of SAM of the boronate moiety.

As shown in FIG. 7, compared to before formation of SAM, an electrode exhibits increased peak separation and decreased peak current after formation of SAM, demonstrating formation of the SAM on the electrode.

EXAMPLE 2

Combination of Biomolecule with Boronate Moiety Immobilized to Reaction Chamber

Glycated hemoglobin was combined with the boronate moiety immobilized to the reaction chamber fabricated in Example 1.

After diluting hemoglobin A1c available from Exocell (hereinafter, referred to as 'HbA1c') 50 times, HbA1c was admixed with a PBS buffer in a ratio of HbA1c:PBS buffer (pH 7)=20 μg:980 μg to produce an HbA1c solution.

An electrode substrate having SAM of the boronate moiety formed in Example 1 was immersed in the prepared HbA1c solution while stirring for 1 hour, so as to combine the boronate moiety with HbA1c.

In order to identify whether HbA1c was coupled to the immobilized boronate moiety, CV was measured. An inner surface of the reaction chamber having HbA1c fixed thereto was washed with a PBS buffer (pH 7), 30 cycles, at an applied potential of 0.5V to −0.15V and a scan rate of 100 mV/s. Using a ferricyanide or ferrocyanide solution (5 mM, pH8), CV of the inner surface of the washed reaction chamber having HbA1c fixed thereto was measured at an applied potential of −0.15V to 0.5V and a scan rate of 100 mV/s.

Figure 8:
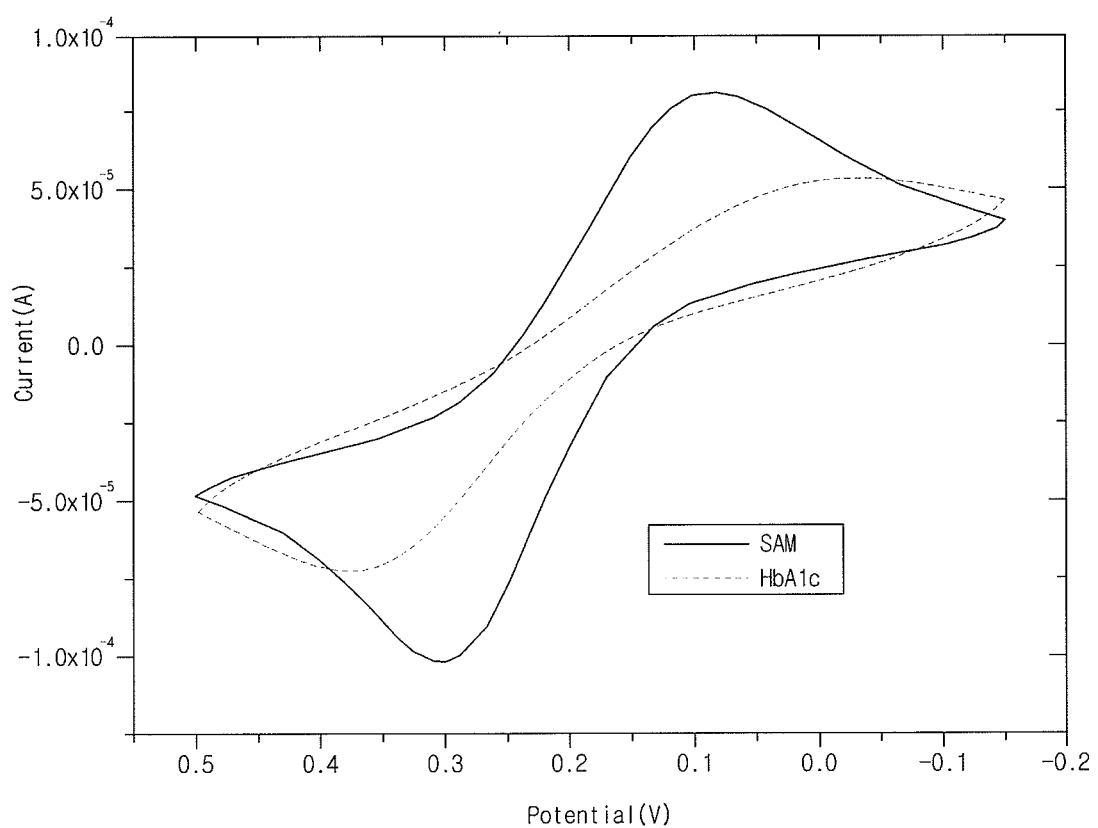
FIG. 8 is CVs measured from an inner surface of a reaction chamber before and after immobilization of glycated hemoglobin HbA1c.

The measured results are shown in FIG. 8. That is, FIG. 8 is CVs measured from the inner surface of the reaction chamber before and after binding of HbA1c to the immobilized boronate moiety.

As shown in FIG. 8, compared to before the binding of HbA1c to the immobilized boronate moiety in the reaction chamber, the inner surface of the reaction chamber after binding of HbA1c exhibits considerably decreased peak current of an electrode, demonstrating binding of HbA1c to the immobilized boronate moiety in the reaction chamber.

EXAMPLE 3

Combination of Target Material with Second Material Generating Electrical Signals After combination of the immobilized boronate moiety in the reaction chamber in Example 2 with the first cis-diol of HbA1c, a second material generating electrical signals was bound to a second cis-diol of HbA1c. As a result, a sandwiched structure wherein boronate moieties are coupled to HbA1c at both ends of the HbA1c was formed.

As a second material, ferrocene boronic acid purchased from Aldrich was dissolved in a PBS buffer (pH 8) to prepare a 1 mM diluted solution and a binding reaction was conducted for 1 hour under stirring.

In order to identify whether HbA1c was coupled to the ferrocene boronic acid, CV was measured. Using a ferricyanide or ferrocyanide solution (5 mM, pH8), CV of the inner surface of the reaction chamber where the ferrocene boronic acid is bound to the immobilized complex of the HbA1c and boronate moiety was measured at an applied potential of −0.15V to 0.5V and a scan rate of 100 mV/s.

Figure 9:
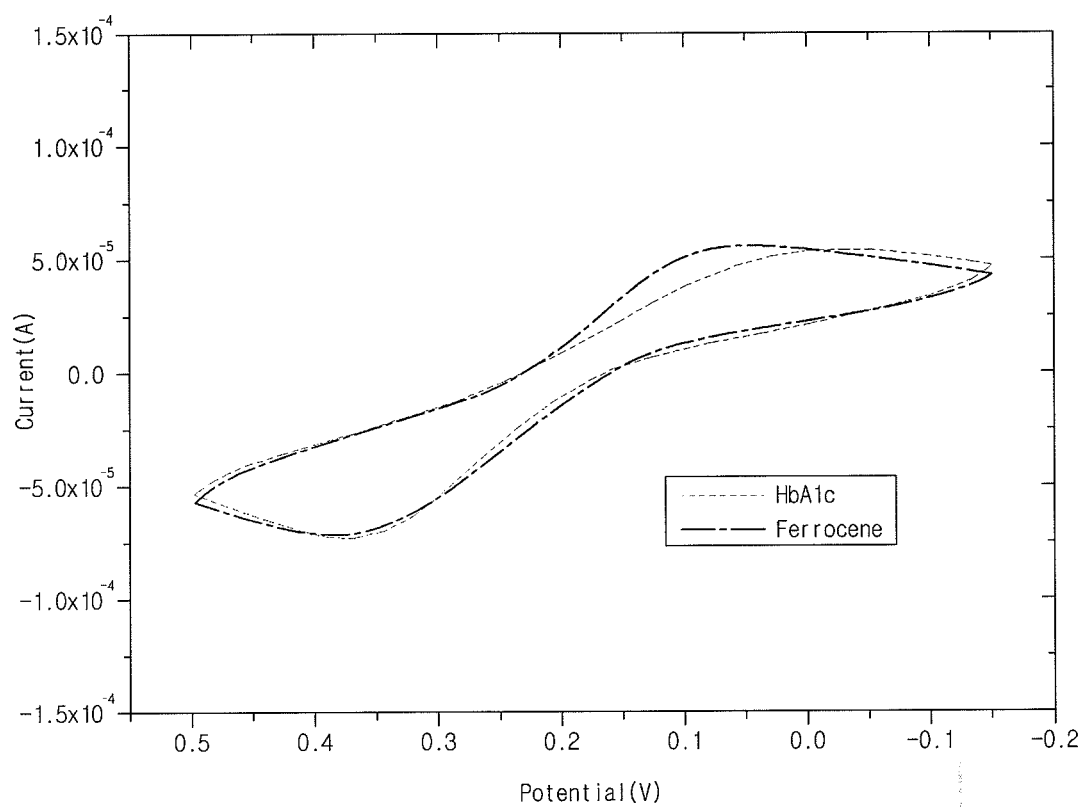
FIG. 9 is CVs measured from an inner surface of a reaction chamber before and after immobilization of ferrocene boronic acid.

The measured results are shown in FIG. 9. That is, FIG. 9 is CVs measured from the inner surface of the reaction chamber before and after fixation of ferrocene boronic acid.

As shown in FIG. 9, compared to the inner surface of the reaction chamber only having HbA1c fixed thereto, the inner surface of the reaction chamber having ferrocene boronic acid as well as HbA1c fixed thereto exhibits considerably increased peak current of an electrode, demonstrating binding of ferrocene boronic acid to the HbA1c which was already coupled to the immobilized first boronate moiety in the reaction chamber.

Figure 10:
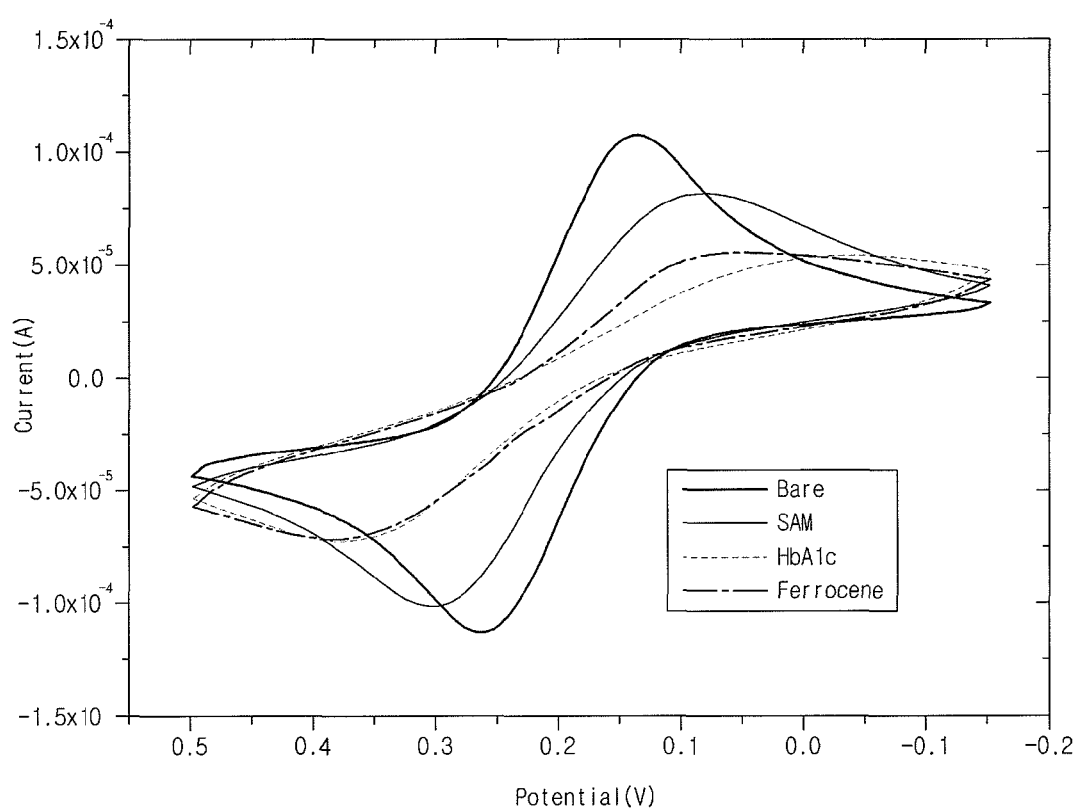
FIG. 10 is a combination of CVs shown in FIGS. 7 to 9.

FIG. 10 is a compilation of CVs shown in FIGS. 7 to 9.

As shown in FIG. 10, after immobilization of a boronate moiety to the inner surface of the reaction chamber (a red line in FIG. 10), after combination of HbA1c with a boronate moiety (a blue line in FIG. 10), and after combination of an electrical signal generating material with HbA1c bound to the immobilized boronate moiety in the reaction chamber (a green line in FIG. 10), respectively, variation in measured CVs was observed. Consequently, existence of target biomolecules of a substance to be analyzed and/or amount thereof may be simply detected.

Although a few embodiments have been shown and described, it would be appreciated by those skilled in the art that substitutions, variations and/or modifications may be made in these embodiments without departing from the principles and spirit of the invention, the scope of which is defined in the claims and their equivalents.

What is claimed is:

1. A micro-fluidic structure suitable for detecting a target material having at least two cis-diol groups, comprising:
    a reaction chamber that contains an immobilized first material, the first material comprising a first boronate moiety which is capable of binding to a cis-diol group of the target material;
    a first chamber that contains a second material comprising a second boronate moiety which is capable of binding to another cis-diol group of the target material, and generating a detectable electrical signal;
    channels through which the chambers are fluid communicative to one another; and
    valves for opening and closing the channels to control the flow of a fluid in the micro-fluidic structure.

2. The micro-fluidic structure according to claim 1, wherein the first boronate moiety is selected from the group consisting of boric acid, boronic acid and a boronate compound.

3. The micro-fluidic structure according to claim 2, wherein the boronate compound is a phenylboronic acid, a boronate ester or a boronate salt.

4. The micro-fluidic structure according to claim 1, wherein an inner surface of the reaction chamber is formed of a material selected from the group consisting of a silicon wafer, silicone, glass, quartz, metal or plastic material.

5. The micro-fluidic structure according to claim 4, wherein the inner surface of the reaction chamber comprises gold, silver, platinum, aluminum or copper.

6. The micro-fluidic structure according to claim 1, wherein the target material is a glycoprotein or a carbohydrate.

7. The micro-fluidic structure according to claim 6, wherein the glycoprotein is selected from the group consisting of glycated hemoglobin, fibrinogen, RNase B, human al-acid glycoprotein, fetuin and horseradish peroxidase.

8. The micro-fluidic structure according to claim 6, wherein the carbohydrate is selected from the group consisting of β-D-glucose, β-D-galactose, β-D-mannose, α-L-fucose, N-acetylgalactosamine, N-acetylglucosamine, N-acetylneuraminic acid and xylose.

9. The micro-fluidic structure according to claim 1, wherein the second material is selected from a group consisting of ferrocene boronate, ferrocene boronate derivatives, boronate ferricyanide, boronate ferrocyanide, a ruthenium complex comprising the second boronate moiety, luminol comprising the second boronate moiety, and lucigenin comprising the second boronate moiety.

10. The micro-fluidic structure according to claim 1, wherein the detectable signal is an electrical signal.

11. The micro-fluidic structure according to claim 1, which further comprises a second chamber which receives a sample containing the target material, said target material having at least two cis-diol groups.

12. The micro-fluidic structure according to claim 1, wherein the first material is coupled to an inner surface of the reaction chamber, or bonded to the outer surface of a bead, a microsphere, a nanoparticle, a membrane, a film, or a porous matrix.

13. A micro-fluidic device based on centrifugal force, comprising:
   a rotational body; and
   the micro-fluidic structure as set forth in claim 1,
   wherein a fluid contained in the micro-fluidic structure flows and moves by centrifugal force generated by rotation of the rotational body.

14. A method for detection of a target material containing at least two cis-diol groups using the micro-fluidic device as set forth in claim 13, comprising:
   providing the micro-fluidic device of claim 13;
   bringing a sample containing the target material that contains at least two cis-diol groups to be in contact with the immobilized first material, thereby one of the at least two cis-diol groups of the target material binds to the boronate moiety of the immobilized first material in the reaction chamber to form an immobilized first material-target material complex;
   bringing the second material to be contact with the target material bound to the immobilized first material, thereby the boronate moiety of the second material binds to another cis-diol group of the at least two cis-diol groups of the target material of the immobilized first material-target material complex; and
   measuring a signal generated from the second material bound to the immobilized first material-target material complex.

15. The method according to claim 14, wherein the first boronate moiety is selected from the group consisting of boric acid, boronic acid, and a boronate compound.

16. The micro-fluidic structure according to claim 15, wherein the boronate compound is a phenylboronic acid.

17. The method according to claim 14, wherein the target material is a glycoprotein or a carbohydrate.

18. The method according to claim 17, wherein the glycoprotein is selected from the group consisting of glycated hemoglobin, fibrinogen, RNase B, human α1-acid glycoprotein, fetuin and horseradish peroxidase.

19. The method according to claim 17, wherein the carbohydrate is selected from the group consisting of β-D-glucose, β-D-galactose, β-D-mannose, α-L-fucose, N-acetylgalactosamine, N-acetylglucosamine, N-acetylneuraminic acid and xylose.

20. The method according to claim 14, wherein the second material is selected from a group consisting of ferrocene boronate, ferrocene boronate derivatives, boronate ferricyanide, boronate ferrocyanide, a ruthenium complex comprising a boronate moiety, luminol comprising a boronate moiety, and lucigenin comprising a boronate moiety.

21. The method according to claim 14, wherein the detectable signal is an electrical signal.

22. The micro-fluidic structure according to claim 1, further comprising a solution chamber that contains a solution for conducting cyclic voltammetry, the solution chamber being fluid communicative with the reaction chamber.

23. The micro-fluidic structure according to claim 22, wherein the solution is a ferricyanide solution or a ferrocyanide solution.

24. The micro-fluidic structure according to claim 22, further comprising:
   a second chamber which supplies a sample containing the target material,
   wherein the second chamber is connected to the solution chamber to provide the sample to the solution chamber.

25. The micro-fluidic structure according to claim 22, wherein the reaction chamber is connected to the solution chamber to receive the sample from the solution chamber.

26. The micro-fluidic structure according to claim 22, wherein the first chamber is fluid communicative with the reaction chamber through the solution chamber.

27. The micro-fluidic structure according to claim 1, wherein the first boronate moiety does not generate a detectable signal.

* * * * *